US008079846B1

(12) United States Patent
  Cookson (10) Patent No.: US 8,079,846 B1
(45) Date of Patent: Dec. 20, 2011

(54) ROTATABLE ELECTRICAL CONNECTOR (75) Inventor: Lyle Cookson, River Edge, NJ (US)

(73) Assignee: Mindray DS USA, Inc., Mahwah, NJ (US)

( * ) Notice: Subject to any disclaimer, the term of this patent is extended or adjusted under 35 U.S.C. 154(b) by 0 days.

(21) Appl. No.: 12/890,416

(22) Filed: Sep. 24, 2010

(51) Int. Cl.
  *H01R 39/00* (2006.01)
(52) U.S. Cl. .......................................... 439/13; 439/909
(58) Field of Classification Search ............... 439/6–13, 439/909
  See application file for complete search history.

(56) References Cited

U.S. PATENT DOCUMENTS

| | | | |
|---|---|---|---|
| 4,802,487 A * | 2/1989 | Martin et al. ................. | 600/463 |
| 5,551,882 A | 9/1996 | Whiteman, Jr. et al. | |
| 5,588,843 A | 12/1996 | Sobhani | |
| 5,690,498 A | 11/1997 | Sobhani | |
| 6,147,416 A | 11/2000 | Mitsuzuka | |
| 6,331,117 B1 | 12/2001 | Brundage | |
| 6,452,668 B1 | 9/2002 | Pratt | |
| 6,630,993 B1 | 10/2003 | Hedges et al. | |
| 6,634,896 B1 * | 10/2003 | Potega ........................... | 439/218 |
| 6,870,608 B2 | 3/2005 | Detweiler et al. | |
| 6,945,803 B2 * | 9/2005 | Potega ........................... | 439/218 |
| 6,981,895 B2 * | 1/2006 | Potega ........................... | 439/578 |
| 7,104,837 B1 | 9/2006 | Huang | |
| 7,187,823 B2 | 3/2007 | Dimsdale et al. | |
| 7,335,053 B2 | 2/2008 | Avevor et al. | |
| 7,474,923 B2 * | 1/2009 | Houben et al. ................ | 439/909 |
| 7,641,480 B1 * | 1/2010 | Hossack et al. ................ | 439/67 |
| 2005/0154262 A1 * | 7/2005 | Banik et al. .................... | 600/179 |
| 2008/0197710 A1 | 8/2008 | Kreitz et al. | |
| 2009/0102313 A1 | 4/2009 | West et al. | |
| 2009/0185658 A1 | 7/2009 | Katcha et al. | |
| 2009/0279899 A1 | 11/2009 | Walewski | |
| 2010/0061730 A1 | 3/2010 | Seki et al. | |
| 2010/0075512 A1 | 3/2010 | Lai | |

FOREIGN PATENT DOCUMENTS

WO        0022380        4/2000

* cited by examiner

*Primary Examiner* — Briggitte R Hammond
(74) *Attorney, Agent, or Firm* — Kory D. Christensen; Stoel Rives LLP (57) ABSTRACT

Various embodiments of a rotatable electrical connector are disclosed herein that may be disposed between a patient sensor and a patient monitor. Various embodiments of rotatable electrical connectors disclosed herein may be utilized to ameliorate some of the problems of cable management in the context of patient monitoring. In various embodiments, the rotatable electrical connector may include a sensor-side power coupling and a monitor-side electrical coupling. The sensor-side power coupling and the monitor-side electrical coupling may be configured such that one electrical coupling is rotatable with respect to the other electrical coupling. A data transmission system may transmit data gathered by a patient sensor to the patient monitor. The data transmission system may comprise a transmitter on the sensor-side connector that is configured to transmit data received from a plurality of sensors to a receiver on the monitor-side connector. Various optical and electromagnetic data transmission technologies may be utilized.

20 Claims, 6 Drawing Sheets

ROTATABLE ELECTRICAL CONNECTOR

TECHNICAL FIELD

The present application relates generally to rotatable electrical connectors. More particularly, the present application relates to systems and methods for using rotatable electrical connectors to electrically couple a plurality of patient sensors to a patient monitor.

DETAILED DESCRIPTION OF PREFERRED EMBODIMENTS

Medical monitoring equipment may be utilized in a variety of circumstances to monitor various patient characteristics. Frequently, a number of sensors may be connected to a patient in order to monitor a variety of physiological characteristics. For example, sensors may be utilized for monitoring physiological parameters of a patient, such as the patient's respiration, blood pressure, blood oxygen, cardiac activity, neurological activity, and/or temperature.

Measurement of each physiological parameter may require a sensor positioned near, on, and/or inside of the patient. Each sensor may be connected to a patient monitor by an electrical cable. Cables attached to sensors may become intertwined or jumbled when a patient moves, during an examination by a medical professional, or at other times during use. Tangled cables may restrict a patient's movement and may cause unintentional disconnection of one or more sensors. Cable management can be a cumbersome and time consuming task for the medical professionals and the patient.

Disclosed herein are various embodiments of a rotatable electrical connector that may be disposed between a plurality of patient sensors and a patient monitor. Various embodiments of rotatable electrical connectors disclosed herein may be utilized to ameliorate some of the problems of cable management in the context of patient monitoring. In various embodiments, the rotatable electrical connector may include a sensor-side power coupling and a monitor-side electrical coupling. The sensor-side power coupling and the monitor-side electrical coupling may be configured such that one electrical coupling is rotatable with respect to the other electrical coupling. In various embodiments, the monitor-side electrical coupling may comprise a circular electrical conductor. The sensor-side electrical coupling may also include a circular conductor in certain embodiments. In other embodiments, the sensor-side electrical coupling may not be circular, but may be configured to remain in electrical contact with a circular monitor-side electrical coupling.

A data transmission system may transmit data gathered by one or more patient sensors to the patient monitor. The data transmission system may comprise a transmitter on the sensor-side connector that is configured to transmit data received from a plurality of sensors to a receiver on the monitor-side connector. The transmitter and receiver may be embodied using a variety of technologies, including optical data transmitters and receivers and electromagnetic data transmission technologies. Optical transmitters/receivers that may be utilized in connection with various embodiments include, for example, infra-red, fiber optic, and the like. Electromagnetic data transmission technologies may include near-field induction, Bluetooth®, Zigbee and the like.

In various embodiments, the sensor-side connector may include a multiplexor. The multiplexor may be configured to receive a plurality of individual data streams from a plurality of sensors and to multiplex the individual data streams into a multiplexed data stream. In embodiments incorporating a multiplexor, a single transmitter and receiver may be configured to transmit data received from a plurality of sensors.

A cable utilized in connection with various embodiments disclosed herein, may include a circuit that provides the cable with a degree of intelligence. In some embodiments, the circuit stores information pertinent to operation of the cable, such as, for example, the type of physiological sensor with which the cable is configured to be coupled, the date of manufacture of the cable, the total time of active usage of the cable, etc. In other or further embodiments, the circuit can be configured to transition among two or more operational states, each of which can correspond to a different sensor configuration. A variety of examples of intelligent cables are disclosed in pending U.S. patent application Ser. No. 12/432, 558, filed Apr. 29, 2009, titled "CABLES FOR PATIENT MONITORING AND RELATED SYSTEMS AND METHODS," which application is incorporated herein by reference in its entirety.

The embodiments of the disclosure will be best understood by reference to the drawings, wherein like elements are designated by like numerals throughout. In the following description, numerous specific details are provided for a thorough understanding of the embodiments described herein. However, those of skill in the art will recognize that one or more of the specific details may be omitted, or other methods, components, or materials may be used. In some cases, operations are not shown or described in detail in order to avoid obscuring various aspects of the disclosure.

Furthermore, the described features, operations, or characteristics may be combined in any suitable manner in one or more embodiments. The order of the steps or actions of the methods described in connection with the embodiments disclosed may be changed as would be apparent to those skilled in the art. Thus, any order in the drawings or detailed description is for illustrative purposes only and is not meant to imply a required order, unless specified to require an order.

Figure 1:
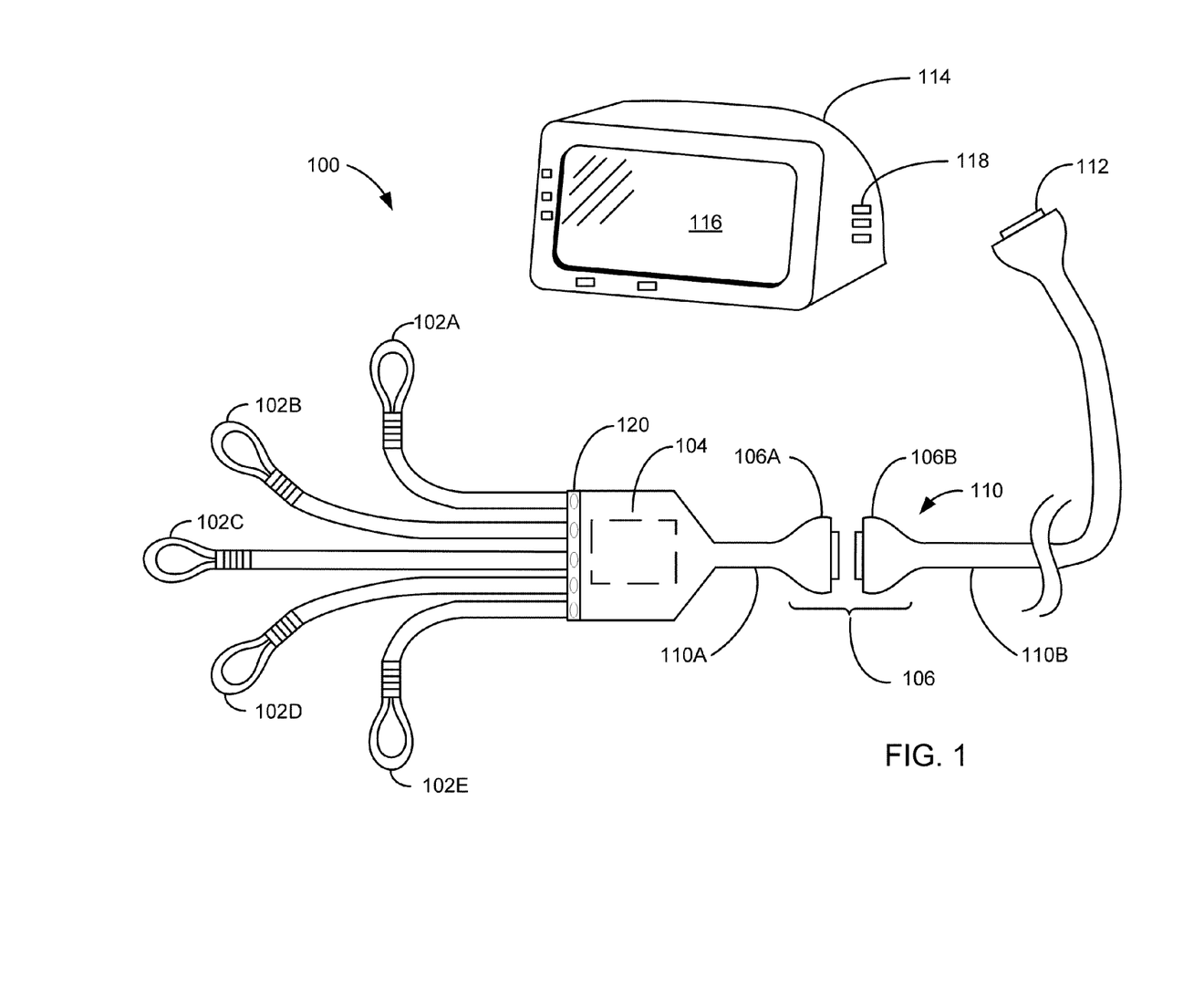
FIG. 1 illustrates a block diagram of one embodiment of a patient monitoring system including a cable comprising a rotatable electrical connector.

FIG. 1 illustrates a patient monitoring system 100 that includes a patient monitor 114 that may display data regarding a patient on a display 116. A plurality of patient sensors (not shown) may gather data and be attached to patient sensor leads 102A-102E. The plurality of patient sensors may gather data regarding one or more patient characteristics (e.g., the patient's respiration, blood pressure, blood oxygen, cardiac activity, neurological activity, and/or temperature). Each of the plurality of patient sensor leads 102A-102E may provide a stream of data regarding the characteristic monitored by the associated sensor.

The data gathered by the sensors may be transmitted via cable 110 to patient monitor 114. The plurality of patient sensor leads 102A-102E may be connected to a plurality of sensor lead inputs 120. In the illustrated embodiment, cable 110 includes a sensor-side cable 110A and a monitor-side cable 110B. As illustrated, one side of sensor-side cable 110A connects to the plurality of patient sensor leads 102A-E, and the other side of sensor-side cable 110A includes a sensor-side connector 106A. Monitor-side cable 110B has a monitor-side connector 106B disposed at one end and a patient monitor interface 112 at the other end. Patient monitor interface 112 may be connected to patient monitor 114 via a patient monitor connector 118.

Monitor-side connector 106B and sensor-side connector 106A form a rotatable electrical connector 106. Sensor-side connector 106A may be rotatable with respect to monitor-side connector 106B. Rotating sensor-side connector 106A with respect to monitor-side connector 106B may help to prevent electrical cables (i.e., sensor leads 102A-102E) from becoming tangled when a patient moves, during an examination by a medical professional, or at some other time. Similarly, rotating sensor-side connector 106A with respect to monitor side-connector 106B may facilitate untangling electrical cables associated with a plurality of sensors.

The individual streams of data provided by each of patient sensor leads 102A-102E may be multiplexed by a multiplexor 104 in order to generate a multiplexed data stream. Additional circuitry may also be provided in order to provide a degree of intelligence to cable 110. In some embodiments, the circuit stores information pertinent to operation of the cable, such as, for example, the type of physiological sensor with which the cable is configured to be coupled, the date of manufacture of the cable, the total time of active usage of the cable, etc.

In the embodiment illustrated in FIG. 1, rotatable electrical connector 106 is disposed between two segments of cable 110 (i.e., sensor-side cable segment 110A and monitor-side cable 110B). Such embodiments may allow for use of the rotatable electrical connections disclosed herein with legacy patient monitors. In other words, the benefits associated with rotatable electrical connectors, as disclosed herein, may be realized without having to replace existing patient monitors. As illustrated in connection with other embodiments discussed below, however, a rotatable monitor-side connector may also be disposed within a patient monitor.

Figure 2:
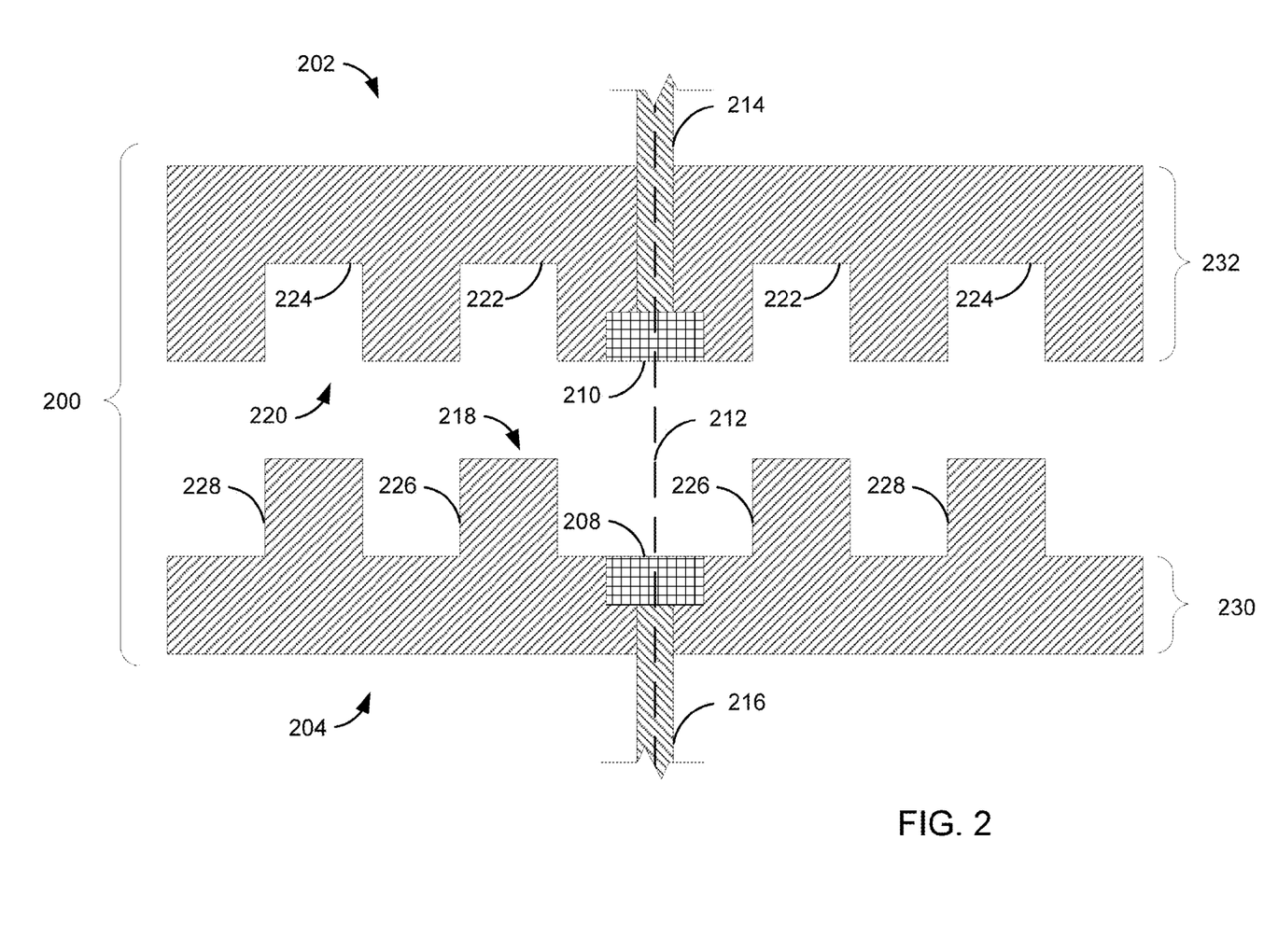
FIG. 2 illustrates a cross-sectional view of one embodiment of a rotatable electrical connector having a power coupling comprising two concentric electrical conductors disposed symmetrically about the circumference of a transmitter.

FIG. 2 illustrates a cross-sectional view of one embodiment of a rotatable electrical connector 200 comprising a sensor-side connector 202 and a monitor-side connector 204. Sensor-side connector 202 and monitor-side connector 204 may be coupled in operation. In the illustrated example, rotatable electrical connector 200 is symmetric about an axis 212. The symmetry about axis 212, as shown in FIG. 2, may allow sensor-side connector 202 to be rotatable with respect to monitor-side connector 204.

Sensor-side connector 202 and monitor-side connector 204 may also comprise a data transmission system. The data transmission system comprises a transmitter 210 and a receiver 208. In embodiments in which bi-directional communication is used, a transceiver may be used in place of each transmitter 210 and receiver 208. In the illustrated embodiment, transmitter 210 and receiver 208 are symmetric with respect to axis 212. Transmitter 210 and receiver 208 may be connected to a plurality of sensor leads (not shown) and a patient monitor (not shown) via cables 214 and 216, respectively.

Transmitter 210 and receiver 208 may be embodied as any form of data transmission system capable of transmitting a data signal between sensor-side connector 202 and monitor-side connector 204. For example, transmitter 210 may be embodied as an optical transmitter, such as an infra-red transmitter or a fiber optic transmitter, or may be embodied as an electromagnetic transmitter, such as a near-field induction transmitter, Zibee transmitter, or a Bluetooth® transmitter. Receiver 208 may be selected to receive the data transmitted by transmitter 210. Transmitter 210 and receiver 208 may, in various embodiments, be configured to communicate a multiplexed data signal.

Each of sensor-side connector 202 and monitor-side connector 204 may comprise complimentary couplings 218 and 220. Complimentary couplings 218 and 220 may be utilized to transmit power from sensor-side connector 202 to monitor-side connector 204, or vice versa. In the illustrated embodiment, complimentary couplings 218 and 220 comprise concentric rings and grooves. A first concentric ring 226 and a second concentric ring 228 may protrude from a base 230 of monitor-side connector 204. A first concentric groove 222 and a second concentric groove 224 may be recessed with respect to a base 232 of sensor-side connector 202. First concentric groove 222 and second concentric groove 224 may be complimentary to first concentric ring 226 and second concentric ring 228.

In a coupled position, electrical conductors disposed on first concentric groove 222 may make electrical contact with electrical conductors disposed on first concentric ring 226. Similarly, in the coupled position, electrical conductors disposed on second concentric groove 224 may abut and make electrical contact with electrical conductors disposed on second concentric ring 228. One electrical conductor (e.g., an electrical conductor (not shown) disposed on first concentric ring 226) may provide a supply voltage, while another electrical conductor (e.g., an electrical conductor (not shown) disposed on second concentric ring 228) may provide an electrical path to ground.

In the coupled position, transmitter 210 and receiver 208 may be aligned with respect to each other and may be disposed in proximity to each other. In the coupled position, transmitter 210 and receiver 208 may communicate a multiplexed data stream from the plurality of sensor leads to the patient monitor.

The symmetry of sensor-side connector 202 and monitor-side connector 204 about axis 212 allows for rotation of sensor-side connector 202 with respect to monitor-side connector 204. Regardless of the rotation of sensor-side connector 202 and monitor-side connector 204, electrical conductors disposed on first concentric ring 226 and/or second concentric ring 228 may remain in electrical contact with electrical conductors disposed in first concentric groove 222 and/or second concentric groove 224. Similarly, regardless of the rotation of sensor-side connector 202 and monitor-side connector 204, the alignment of transmitter 210 and receiver 208 remains unchanged.

Figure 3:
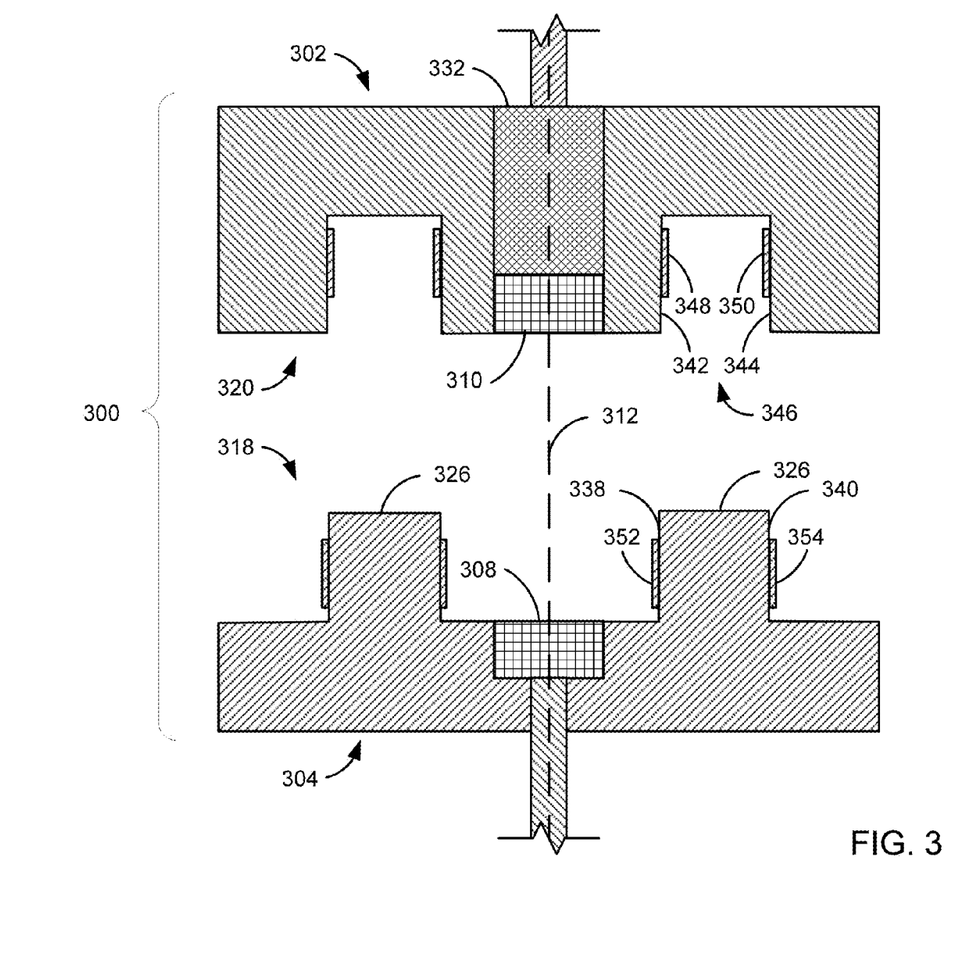
FIG. 3 illustrates a cross-sectional view of one embodiment of a rotatable electrical connector having a power coupling comprising a pair of circular electrical conductors disposed symmetrically about the circumference of a transmitter.

FIG. 3 illustrates a cross-sectional view of one embodiment of a rotatable electrical connector 300 having a power coupling comprising a pair of circular electrical conductors disposed symmetrically about the circumference of a transmitter. A sensor-side connector 302 may comprise a transmitter 310, while a monitor-side connector 304 may comprise a receiver. Transmitter 310 may be in electrical communication with and receive data from a multiplexor 332. Multiplexor 332 may be configured to generate a multiplexed data stream comprising a plurality of individual data streams received from a plurality of sensors (not shown). Use of multiplexor 332 may allow transmitter 310 and a receiver 308 to transmit data received from the plurality of sensors using a single data transmission channel.

A monitor-side complimentary coupling 318 and a sensor-side complimentary coupling 320 may be configured to couple and to transfer power in the coupled position. In the coupled position, ring 326 may be received by groove 346. Sensor-side electrical conductors 348 and 350 may be disposed on an interior edge 342 of groove 346 and an exterior edge 344 of groove 346, respectively. In the coupled position, electrical conductors 348 and 350 may be brought into contact with electrical conductors 352 and 354 disposed on an interior edge 338 of ring 326 and an exterior edge 340 of ring 326, respectively. One pair of electrical conductors (e.g., electrical conductors 348 and 352) may provide a supply voltage, while the other pair of electrical conductors (e.g., electrical conductors 350 and 354) may provide an electrical path to ground.

Figure 4:
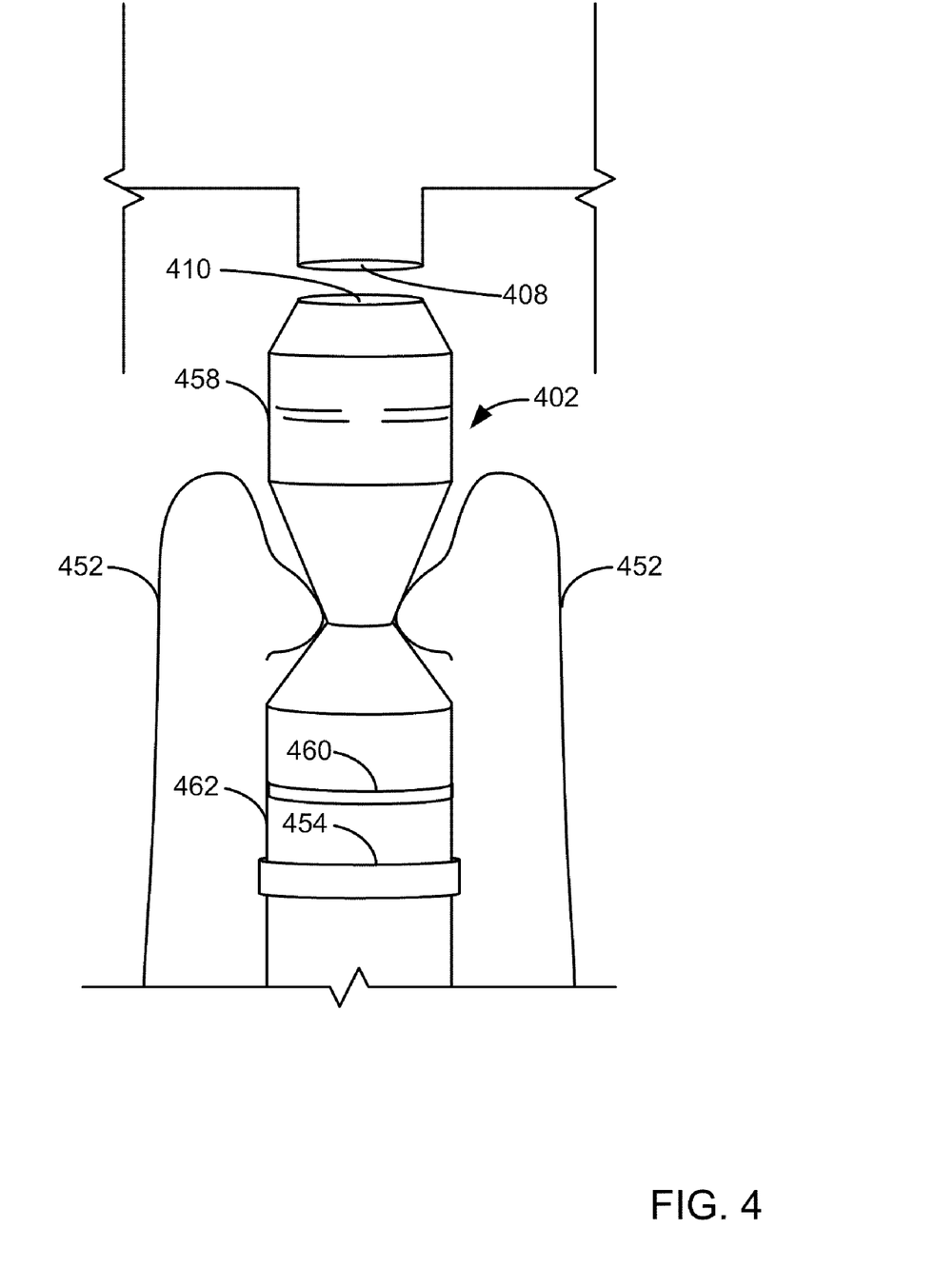
FIG. 4 illustrates a perspective view of one embodiment of a rotatable electrical connector including a tip-ring-sleeve connector.

FIG. 4 illustrates a perspective view of one embodiment of a rotatable electrical connector including a tip-ring-sleeve connector. Like the embodiments discussed above, the embodiment illustrated in FIG. 4 includes a transmitter 410 and a receiver 408, which may be utilized for communicating a multiplexed signal comprising a plurality of data streams received from a plurality of sensors (not shown).

Sensor-side connector 402 includes a tip section 458, a ring section 460, and a sleeve section 462. In the illustrated embodiment, sensor-side connector 402 may be referred to as a tip-ring-sleeve connector ("TRS Connector"). Each section of the TRS Connector may serve a different function. In one embodiment, tip section 458 may function as an electrical conductor. In a coupled position, as shown in FIG. 4, tip section 458 may be in electrical communication with one or more electrical conductors 452. Electrical conductors 452 may also hold sensor-side connector 402 in position. Ring section 460 electrically separates tip section 458 from sleeve section 462. Ring section 460 may comprise an electrical insulator. Sleeve section 462 may also serve as an electrical connector. An electrical connector 454 may be in electrical contact with sleeve section 462. Tip section 458 and sleeve section 462 may draw power from electrical connectors 452 and 454. Power drawn by electrical connectors 452 and 454 may be used to power a multiplexor (not shown) and transmitter 410. In addition, power may also be provided to one or more of the plurality of sensors (not shown) in electrical communication with sensor-side connector 402. Various embodiments may utilize one or more TRS Connectors to provide a mechanical coupling between a sensor-side connector and a monitor-side connector.

Figure 5A:
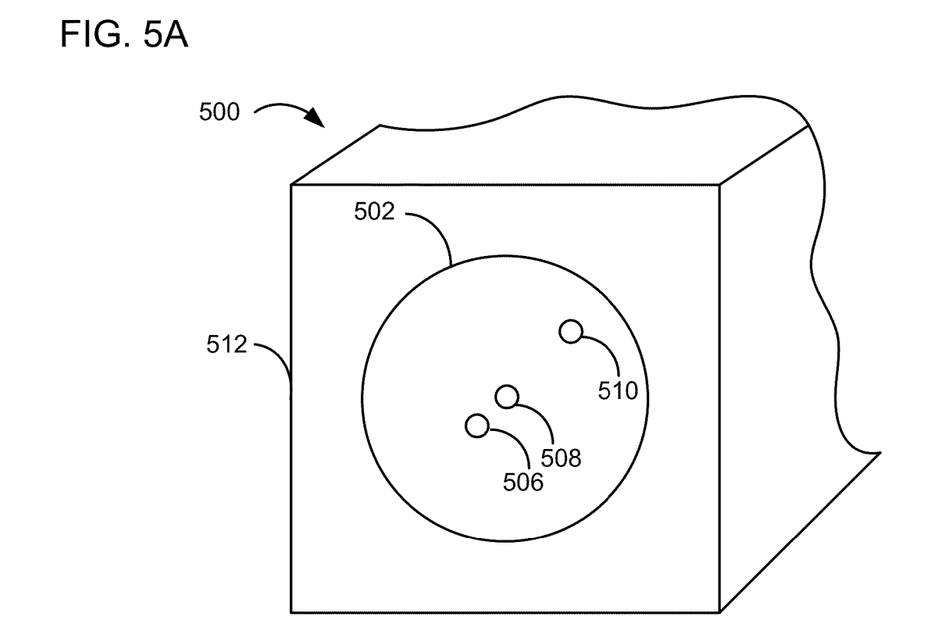
FIGS. 5A and 5B illustrate one embodiment of a monitor-side connector that may be utilized in connection with a sensor-side connector illustrated in FIG. 5C.
Figure 5B:
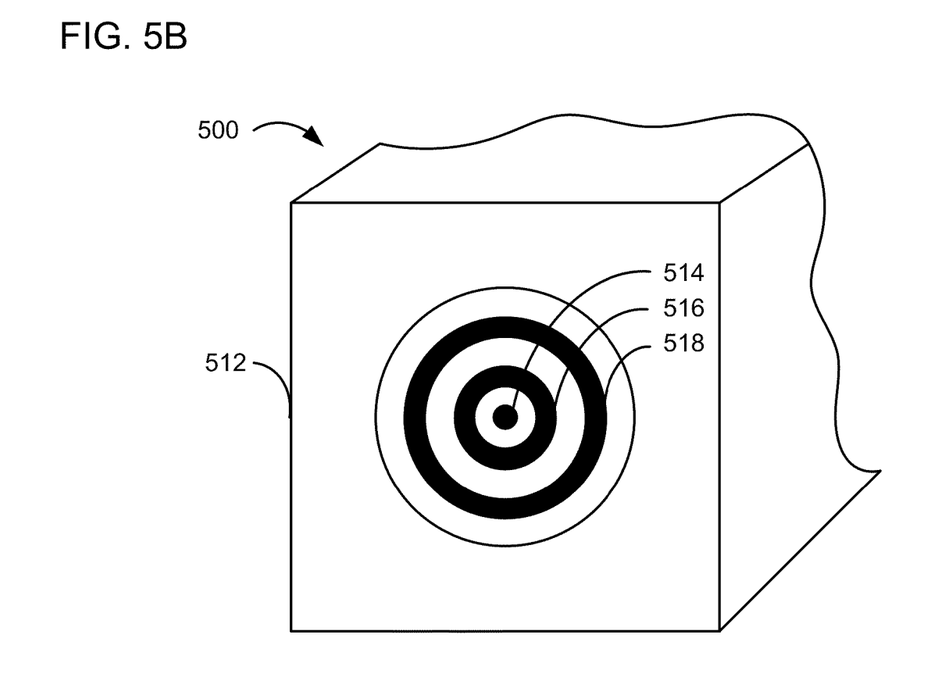
Figure 5C:
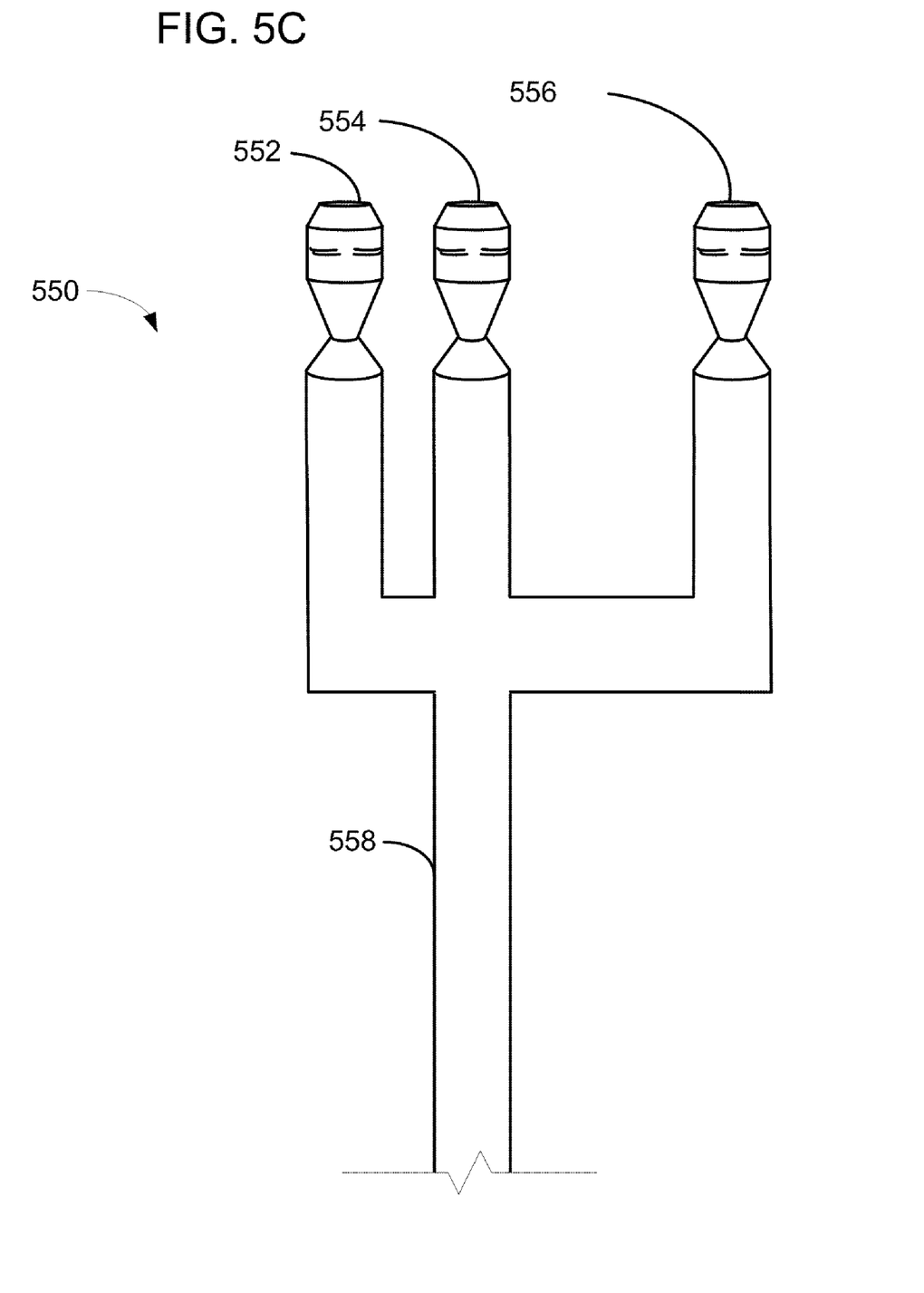

FIGS. 5A and 5B illustrate one embodiment of a monitor-side connector 500 that may be utilized in connection with a sensor-side connector 550, as shown in FIG. 5C. Monitor-side connector 500 may include a stationary portion 512 and a rotatable cover 502. Rotatable cover 502 may include apertures 506, 508, and 510, which may be configured to receive protrusions of sensor-side connector 550.

FIG. 5B illustrates monitor-side connector 500 with rotatable cover 502 removed. As illustrated in FIG. 5B, an aperture 514 may be disposed in the center of two concentric circles 516 and 518. Aperture 514 may be configured to receive a first protrusion of sensor-side connector 550 in a coupled position. A receiver (not shown) may be disposed within aperture 514. Concentric circles 516 and 518 may comprise grooves into which a protrusion of sensor-side connector 550 may be received. Concentric circles 516 and 518 may contain electrical conductors (not shown). In the coupled position, protrusions of sensor-side connector 550 may be maintained in electrical communication with the electrical conductors associated with concentric circles 516 and 518. In various embodiments the electrical conductors associated with circles 516 and 518 may provide a supply voltage and an electrical path to ground.

Sensor-side connector 550, as shown in FIG. 5C, includes three protrusions 552, 554, and 556. Protrusion 554 may be configured to be received within aperture 514. Protrusion 554 may include a transmitter (not shown) that may be configured to communicate with the receiver disposed within aperture 514. Protrusions 552 and 556 may be received within concentric circles 516 and 518, respectively, in a coupled position. A cable 558 may be utilized to connect to a plurality of sensors (not shown). Sensor-side connector 550 may be configured such that protrusions 552, 554, and 556 are not symmetrical, and accordingly, sensor-side connector 550 can only be received by aperture 514 and concentric circles 516 and 518 in a particular orientation.

Those having skill in the art will recognize that many changes may be made to the details of the above-described embodiments without departing from the underlying principles disclosed herein. The scope of the present invention should, therefore, be determined only by the following claims.

I claim:

1. A cable comprising a rotatable electrical connection for electrically connecting a patient monitor to a plurality of patient sensors, comprising:
    a sensor-side connector configured to connect to a plurality of patient sensors, comprising:
        a multiplexor configured to multiplex a plurality of signals received from the plurality of patient sensors to generate a multiplexed signal;
        a transmitter in communication with the multiplexor and configured to transmit the multiplexed signal;
        a sensor-side rotatable power coupling;
    a monitor-side connector configured to rotatably couple to the sensor-side connector, the monitor-side connector comprising:
        a receiver configured to receive the multiplex signal;
        a monitor-side power coupling, comprising:
            a first monitor-side circular electrical conductor disposed symmetrically about a circumference of the receiver and configured to provide electrical power to the sensor-side rotatable power coupling.

2. The rotatable electrical connector of claim 1, wherein the transmitter comprises an optical transmitter and the receiver comprises an optical receiver.

3. The rotatable electrical connector of claim 2, wherein the transmitter comprises at least one of an infrared transmitter and a fiber optic transmitter.

4. The rotatable electrical connector of claim 1, wherein the transmitter comprises an electromagnetic transmitter and the receiver comprises an electromagnetic receiver.

5. The rotatable electrical connector of claim 4, wherein the transmitter comprises a near-field induction transmitter and the receiver comprises a near-field induction receiver.

6. The rotatable electrical connector of claim 1, wherein the sensor-side connector is arbitrarily rotatable with respect to the monitor-side connector.

7. The rotatable electrical connector of claim 1, wherein the sensor-side connector further comprises a plurality of sensor lead inputs, each sensor lead input providing at least one signal of the plurality of signals.

8. The rotatable electrical connector of claim 1, further comprising a mechanical coupling to rotatably couple the sensor-side connector to the monitor-side connector.

9. The rotatable electrical connector of claim 8, wherein the mechanical coupling comprises a tip-ring-sleeve connector.

10. The rotatable electrical connector of claim 1, wherein the sensor-side connector comprises a tip-sleeve (TS) connector, and wherein the monitor-side connector comprises a TS connector jack configured to receive the TS connector, and thereby rotatably couple the sensor-side connector to the monitor-side connector.

11. The rotatable electrical connector of claim 1, wherein the sensor-side rotatable power coupling comprises a sensor-side circular electrical conductor disposed symmetrically about a circumference of the transmitter.

12. The rotatable electrical connector of claim 11, wherein the first monitor-side circular electrical conductor and the sensor-side circular electrical conductor comprise a ring and a groove, and wherein the groove receives the ring in a coupled configuration.

13. The rotatable electrical connector of claim 11, further comprising a second monitor-side circular electrical conductor, wherein the sensor-side power coupling comprises a first sensor-side circular electrical conductor and a second sensor-side circular electrical conductor, and wherein the first monitor-side circular electrical conductor is in electrical communication with the first sensor-side circular electrical conductor and the second monitor-side circular electrical conductor is in electrical communication with the second monitor-side circular conductor in a coupled configuration.

14. A system for electrically connecting a patient monitor to a plurality of patient sensors, comprising:
a cable comprising:
a multiplexor configured to multiplex a plurality of signals received from the plurality of patient sensors to generate a multiplexed signal;
a transmitter in communication with the multiplexor and configured to transmit the multiplexed signal;
a sensor-side rotatable power coupling; and
a patient monitor comprising:
a monitor-side connector configured to rotatably couple to the sensor-side connector, the monitor-side connector comprising:
a receiver configured to receive the multiplexed signal;
a monitor-side power coupling, comprising:
a first monitor-side circular electrical conductor disposed symmetrically about a circumference of the receiver and configured to provide electrical power to the sensor-side rotatable power coupling.

15. The system of claim 14, wherein the transmitter comprises an optical transmitter and the receiver comprises an optical receiver.

16. The system of claim 14, wherein the transmitter comprises a near-field induction transmitter and the receiver comprises a near-field induction receiver.

17. The system of claim 14, wherein the sensor-side connector is arbitrarily rotatable with respect to the monitor-side connector.

18. The system of claim 14, further comprising a mechanical coupling to rotatably couple the sensor-side connector to the monitor-side connector.

19. The system of claim 18, wherein the mechanical coupling comprises a tip-ring-sleeve connector.

20. A method for electrically connecting a patient monitor to a plurality of patient sensors, comprising:
connecting a plurality of patient sensors to a sensor-side connector;
connecting a patient monitor to a monitor-side connector;
generating a multiplexed signal by multiplexing a plurality of signals received from the plurality of patient sensors;
transmitting the multiplexed signal from the sensor-side connector to the monitor-side connector;
coupling a sensor-side rotatable power coupling to a monitor-side power coupling;
providing electrical power from the monitor-side power coupling to the sensor-side rotatable power coupling; and
rotating the sensor-side connector with respect to the monitor-side connector.

* * * * *